US012691274B2

(12) United States Patent
Toh et al.

(10) Patent No.: US 12,691,274 B2
(45) Date of Patent: Jul. 28, 2026

(54) CATHETER PRIMING DEVICES, SYSTEMS AND METHODS

(71) Applicant: Becton, Dickinson and Company, Franklin Lakes, NJ (US)

(72) Inventors: Say Kiong Toh, Bedok (SG); Chun Keat Ooi, Castletroy (IE)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 18/208,728

(22) Filed: Jun. 12, 2023

(65) Prior Publication Data

US 2023/0321426 A1      Oct. 12, 2023

Related U.S. Application Data

(63) Continuation of application No. 16/558,871, filed on Sep. 3, 2019, now Pat. No. 11,724,087.

(Continued)

(51) Int. Cl.
*A61M 39/22*          (2006.01)
*A61M 25/06*          (2006.01)
(Continued)

(52) U.S. Cl.
CPC ...... *A61M 39/225* (2013.01); *A61M 25/0606* (2013.01); *A61M 39/10* (2013.01); *A61M 39/24* (2013.01); *A61M 2039/0018* (2013.01); *A61M 2039/1077* (2013.01); *A61M 2039/226* (2013.01); *A61M 2039/2413* (2013.01); *A61M 2039/246* (2013.01); *A61M 2039/248* (2013.01)

(58) Field of Classification Search
CPC ............... A61M 39/225; A61M 39/10; A61M 25/0606; A61M 2005/1402; A61M 2005/1403; A61M 39/24; A61M 2039/0018; A61M 2039/1077; A61M 2039/2413; A61M 2039/246; A61M 2039/248; A61M 5/148; A61M 5/152
See application file for complete search history.

(56) References Cited

U.S. PATENT DOCUMENTS 4,034,754  A      7/1977   Virag
5,078,688  A      1/1992   Lobodzinski et al.
(Continued)

FOREIGN PATENT DOCUMENTS

CN          203915611 U      11/2014
CN          105164016 A      12/2015
(Continued)

*Primary Examiner* — Kevin C Sirmons
*Assistant Examiner* — Antarius S Daniel
(74) *Attorney, Agent, or Firm* — Kirton McConkie; Whitney Blair; Kevin Stinger

(57)          ABSTRACT

A catheter priming apparatus may include a barrier forming a reservoir. Fluid may be disposed within the reservoir. A support structure may be disposed within the barrier. The support structure may include an opening extending through the support structure and a connector configured to couple the catheter priming apparatus to a catheter system. A one-way valve may be coupled to the support structure and configured to allow the fluid to flow out of the reservoir through the connector in response to compression of a portion of the barrier aligned with the opening.

20 Claims, 8 Drawing Sheets

Related U.S. Application Data

(60) Provisional application No. 62/729,804, filed on Sep. 11, 2018.

(51) Int. Cl.

| | | |
|---|---|---|
| *A61M 39/10* | (2006.01) | |
| *A61M 39/24* | (2006.01) | |
| *A61M 39/00* | (2006.01) | |

(56) References Cited

U.S. PATENT DOCUMENTS

| | | | | |
|---|---|---|---|---|
| 5,261,459 | A * | 11/1993 | Atkinson | A61M 39/24 |
| | | | | 137/846 |
| 5,284,481 | A * | 2/1994 | Soika | A61M 5/152 |
| | | | | 206/370 |
| 7,024,836 | B2 | 4/2006 | Powell et al. | |
| 7,322,961 | B2 * | 1/2008 | Forrest | A61M 5/152 |
| | | | | 604/93.01 |
| 8,412,300 | B2 | 4/2013 | Sonderegger | |
| 2002/0198560 | A1 | 12/2002 | Boyle et al. | |
| 2004/0242996 | A1 | 12/2004 | Trombley et al. | |
| 2006/0293560 | A1 | 12/2006 | Nguyen et al. | |
| 2009/0062766 | A1 * | 3/2009 | Howlett | A61M 39/20 |
| | | | | 604/411 |
| 2010/0174252 | A1 | 7/2010 | Tanghoej et al. | |
| 2011/0015564 | A1 | 1/2011 | Bonnette et al. | |
| 2011/0044850 | A1 | 2/2011 | Solomon | |
| 2011/0213341 | A1 | 9/2011 | Solomon et al. | |
| 2015/0367044 | A1 | 12/2015 | Streitmann et al. | |
| 2016/0136398 | A1 * | 5/2016 | Heilman | A61M 25/0108 |
| | | | | 604/9 |
| 2017/0239443 | A1 | 8/2017 | Edward et al. | |
| 2017/0367861 | A1 | 12/2017 | Kölbel | |
| 2018/0239370 | A1 * | 8/2018 | Perry, Jr. | A61M 5/3134 |

FOREIGN PATENT DOCUMENTS

| | | |
|---|---|---|
| CN | 106620939 A | 5/2017 |
| JP | 109308687 A | 12/1997 |
| JP | 2000084033 A | 3/2000 |
| JP | 2011518024 A | 6/2011 |
| JP | 2012517328 A | 8/2012 |
| JP | 2013529116 A | 7/2013 |
| JP | 2018520784 A | 8/2018 |
| WO | 199213584 A1 | 8/1992 |
| WO | 2004108192 A1 | 12/2004 |
| WO | 2009117663 A2 | 9/2009 |
| WO | 2010002808 A1 | 1/2010 |
| WO | 2016205779 A2 | 12/2016 |

* cited by examiner

CATHETER PRIMING DEVICES, SYSTEMS AND METHODS

RELATED APPLICATIONS

This application is a continuation of U.S. patent application Ser. No. 16/558,871, filed Sep. 3, 2019, and entitled CATHETER PRIMING DEVICES, SYSTEMS AND METHODS, which claims the benefit of U.S. Provisional Patent Application No. 62/729,804, filed on Sep. 11, 2018, and entitled CATHETER PRIMING DEVICES, SYSTEMS AND METHODS, which are incorporated herein in their entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient. In some instances, catheters and attached tubing sets that are used for fluid infusion may be primed prior to insertion into vasculature of the patient to remove air. If air bubbles are allowed to enter the vasculature of the patient, an embolism may form, which may cause serious injury to the patient.

The subject matter claimed herein is not limited to embodiments that solve any disadvantages or that operate only in environments such as those described above. Rather, this background is only provided to illustrate one example technology area where some implementations described herein may be practiced.

BRIEF SUMMARY

The present disclosure relates generally to catheter priming devices, systems, and methods. In some embodiments, a fluid storage unit may be coupled to a catheter system to facilitate priming of the catheter system. In some embodiments, the fluid storage unit may eliminate a need to use of a pre-filled syringe or an IV drip chamber to prime the catheter system. In some embodiments, after the fluid storage unit is coupled to the catheter system, the fluid storage unit may be activated to release fluid within the fluid storage unit into the catheter system and to prime the catheter system. In some embodiments, the fluid storage unit may be activated prior to catheterization or insertion of the catheter system into vasculature of a patient.

In some embodiments, the catheter system may include a catheter assembly, which may include a catheter hub and a catheter, which may extend distally from the distal end of the catheter hub. In some embodiments, the catheter may include a peripheral intravenous catheter ("PIVC"). In some embodiments, the catheter hub may include a distal end, a proximal end, and a lumen extending between the distal end and the proximal end.

In some embodiments, the catheter hub may include a side port. In some embodiments, the catheter system may include an extension tube, which may include a distal end and a proximal end. In some embodiments, the distal end of the extension tube may be coupled to the side port.

In some embodiments, the catheter system may include an adapter coupled to the proximal end of the extension tube. In some embodiments, the adapter may include a Y-adapter or another suitable adapter. In some embodiments, the catheter system may include the fluid storage unit. In some embodiments, the fluid storage unit may be coupled to the adapter.

In some embodiments, the fluid storage unit may include a barrier forming a reservoir. In some embodiments, the barrier may include a film. In some embodiments, the barrier may be constructed of foil. In some embodiments, the fluid may be disposed within the reservoir. In some embodiments, the fluid may include a saline solution or another suitable priming fluid.

In some embodiments, the fluid storage unit may include a support structure disposed within the barrier and/or the reservoir. In some embodiments, the support structure may include an opening extending therethrough. In some embodiments, the opening may be about a size of a human thumb, which may facilitate pinching of the fluid storage unit by a human hand to compress the fluid storage unit. In some embodiments, the support structure may include a ring or another suitable shape. In some embodiments, the support structure may be rigid. In some embodiments, the support structure may include one or more polymers.

In some embodiments, the support structure may include a connector configured to couple the fluid storage unit to the catheter system. For example, the connector may be configured to couple the fluid storage unit to the adapter. In some embodiments, the connector may include a male or female luer fitting.

In some embodiments, the fluid storage unit may include a one-way valve, which may be coupled to the support structure. In some embodiments, the one-way valve may prevent unintended fluid suck-back into the reservoir after the fluid storage unit is compressed. In some embodiments, the one-way valve may be configured to allow the fluid to flow out of the reservoir and through the connector in response to compression of a portion of the barrier aligned with the opening. In some embodiments, the fluid is released from the reservoir and flows through the connector in response to the compression exceeding a threshold value but not when the compression is below the threshold value.

In some embodiments, the support structure may reduce compression of another portion of the barrier. In some embodiments, an outer diameter of the portion of the barrier aligned with the opening may be less than an outer diameter of the other portion of the barrier. In some embodiments, the portion of the barrier aligned with the opening may be disposed inwardly with respect to the other portion of the barrier, which may be disposed around the portion of the barrier aligned with the opening. In some embodiments, the inward positioning of the portion of the barrier aligned with the opening may prevent accidental activation of the fluid storage unit during transportation.

In some embodiments, the barrier may include an aperture. In some embodiments, the fluid storage unit may include a seal, which may be coupled to a spring. In some embodiments, in response to compression of the barrier, the fluid may force the seal distally to open the aperture and compress the spring. In some embodiments, the spring may be configured to return the seal to a position sealing the aperture in response to ceasing of compression of the barrier.

In some embodiments, the seal may include a ball. In some embodiments, the fluid storage unit may include a washer, which may be coupled to the barrier. In some embodiments, a distal end of the spring may be coupled to the seal. In some embodiments, a proximal end of the spring may be coupled to the washer. In some embodiments, in response to compression of the barrier, the fluid may flow through the aperture, around the seal and the spring, and through the washer. In some embodiments, the seal may be moved distally such that the fluid is released from the reservoir through the aperture in response to compression of the barrier exceeding a threshold value but not when compression of the barrier is below the threshold value.

In some embodiments, a distal end of the barrier may include a connecting portion configured to couple to the catheter system. In some embodiments, an outer surface of the connecting portion may abut an inner surface of the adapter, creating a fluid seal. In some embodiments, the outer surface of the connecting portion and/or the inner surface of the adapter may be tapered. In some embodiments, the outer surface of the connecting portion and/or the inner surface of the adapter may be tapered at an angle within a range of about 5° to 10°. In some embodiments, the outer surface of the connecting portion and/or the inner surface of the adapter may be tapered at an angle of about 6°. In some embodiments, the outer surface of the connecting portion may be tapered outwardly in a distal direction, and the inner surface of the adapter may be tapered inwardly in a proximal direction, helping to create the fluid seal. Alternatively, in some embodiments, the outer surface of the connecting portion may be tapered inwardly in a distal direction, and the inner surface of the adapter may be tapered outwardly in a proximal direction, helping to create the fluid seal.

In some embodiments, the fluid storage unit may include a duckbill valve coupled to the barrier. In some embodiments, the duckbill valve may be configured to open in response to compression of the barrier to allow the fluid to flow out of the fluid storage unit. In some embodiments, a first flap and a second flap of the duckbill valve may be configured to contact each other and seal the fluid storage unit in response to ceasing of compression of the barrier.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DETAILED DESCRIPTION

Figure 1A:
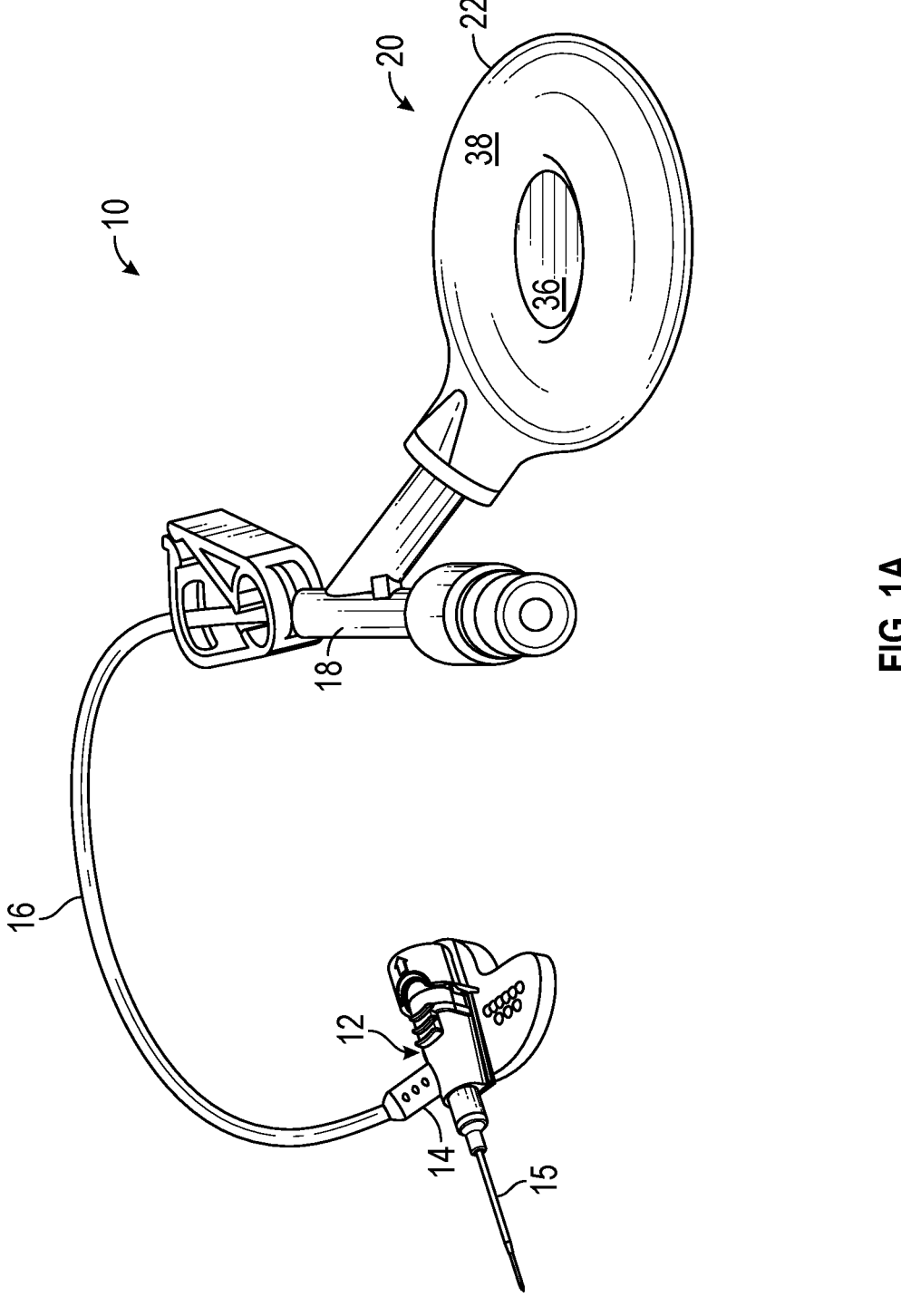
FIG. 1A is an upper perspective view of an example catheter system having an example fluid storage unit, according to some embodiments.
Figure 1B:
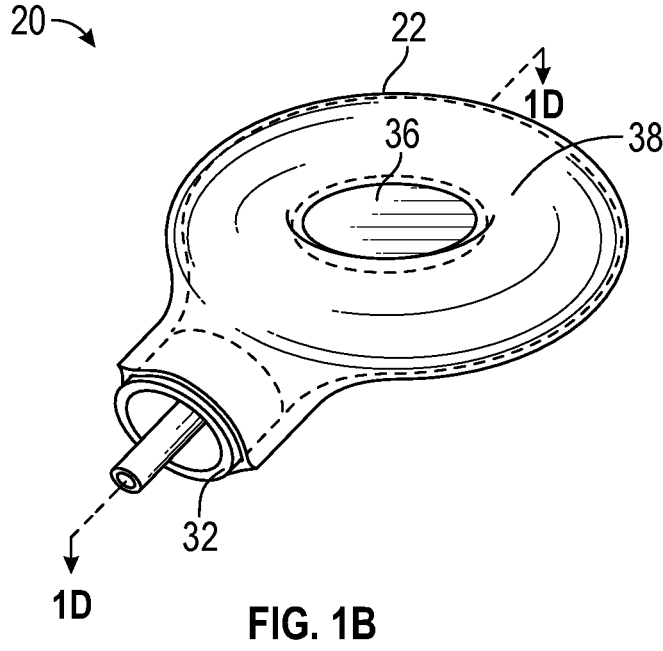
FIG. 1B is an upper perspective view of the fluid storage unit of FIG. 1A, according to some embodiments.
Figure 1C:
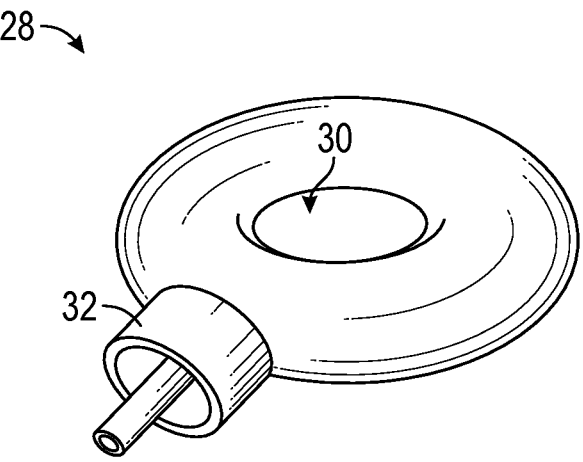
FIG. 1C is an upper perspective view of an example support structure of the fluid storage unit of FIG. 1A, according to some embodiments.
Figure 1D:
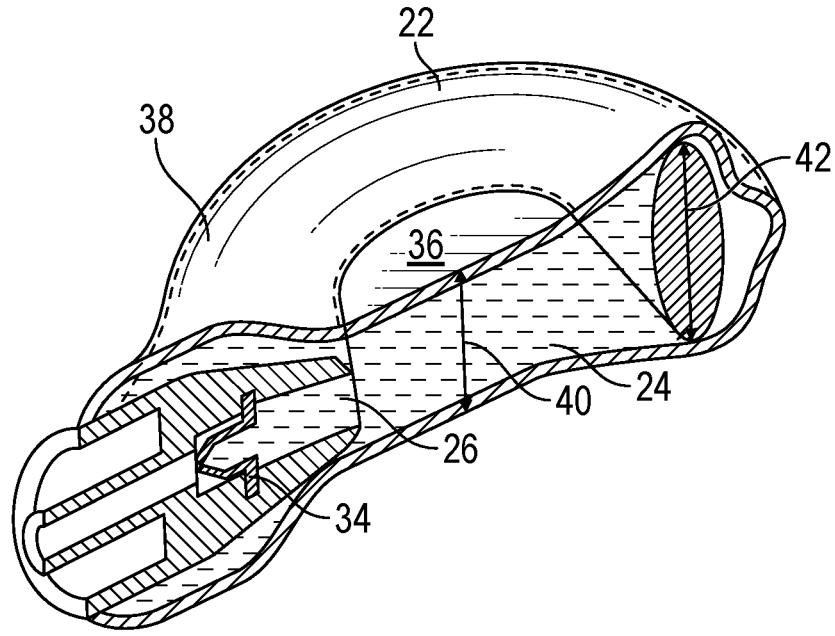
FIG. 1D is a cross-sectional view of the fluid storage unit of FIG. 1B along the line 1D-1D of FIG. 1B, according to some embodiments.

Referring now to FIG. 1A-1D, in some embodiments, a catheter system 10 may include a catheter assembly, which may include a catheter hub 12. In some embodiments, the catheter hub 12 may include a distal end, a proximal end, and a lumen extending between the distal end and the proximal end. In some embodiments, the catheter hub 12 may include a side port 14.

In some embodiments, the catheter assembly may include a catheter 15, which may be secured within and/or extend distally from the distal end of the catheter hub 12. In some embodiments, the catheter 15 may include a PIVC. In some embodiments, the catheter assembly may include a closed IV catheter assembly, such as, for example, the Becton Dickinson NEXIVA™ Closed IV Catheter System or the Becton Dickinson NEXIVA™ DIFFUSICS™ Closed IV Catheter System. In some embodiments, the catheter assembly may include an extension tube 16, which may include a distal end and a proximal end. In some embodiments, the catheter assembly may include another type of catheter assembly, such as, for example, a non-integrated catheter assembly or a catheter assembly without the extension tube 16.

In some embodiments, the distal end of the extension tube 16 may be coupled to the side port 14. In some embodiments, the catheter assembly may include an adapter 18, which may be coupled to the proximal end of the extension tube 16. In some embodiments, the adapter 18 may include a Y-adapter or another suitable adapter.

In some embodiments, the catheter system 10 may include a fluid storage unit 20, which may be coupled to the adapter 18. In some embodiments, the fluid storage unit 20 may be activated by compression to release fluid within the fluid storage unit 20 and may facilitate priming of the catheter system 10.

In some embodiments, priming of the catheter system 10 may achieve a bubble-free fluid pathway of the catheter system 10. In some embodiments, the fluid pathway of the catheter system 10 may include one or more of the following: the catheter 15, the catheter hub 12, the extension tube 16, and the adapter 18. In some embodiments, the priming of the catheter assembly 10 may occur prior to catheterization or insertion of the catheter assembly into vasculature of a patient. In some embodiments, in response to compression or squeezing of the fluid storage unit 20, the fluid 26 may flow from the fluid storage unit 20 through the fluid pathway of the catheter system 10. In some embodiments, the fluid storage unit 20 may eliminate a need to use of a pre-filled syringe or an IV drip chamber to prime the catheter system 10. In some embodiments, the fluid 26 may flow through fluid pathway in response to compression of the fluid storage unit 20 exceeding a threshold value but not when compression of the fluid storage unit 20 is below the threshold value.

In some embodiments, the fluid storage unit 20 may include a barrier 22 forming a reservoir 24. In some embodiments, the barrier 22 may include a film. In some embodiments, the barrier 22 may be constructed of foil. In some embodiments, the fluid storage unit 20 may be constructed of a flexible or semi-flexible material, which may facilitate compression of the fluid storage unit 20. In some embodiments, the fluid storage unit 20 may be constructed of plastic. In some embodiments, the fluid 26 may be disposed within the reservoir 24. In some embodiments, the fluid 26 may include a saline solution or another suitable priming fluid.

In some embodiments, the fluid storage unit 20 may include a support structure 28 disposed within the barrier 22 and/or the reservoir 24. In some embodiments, the support structure 28 may be enclosed within the barrier 22. In some embodiments, the support structure 28 may include an opening 30 extending therethrough. In some embodiments, the opening 30 may be about a size of a human thumb, which may facilitate pinching of the fluid storage unit 20 by a human hand to compress the fluid storage unit 20. In some embodiments, the opening 30 may be positioned about in a middle of the fluid storage unit 20 or at another position. In some embodiments, the support structure 28 may include a ring or another suitable shape. In some embodiments, the reservoir 24 may be at least partially disposed within the opening 30.

In some embodiments, the support structure 28 may be rigid. In some embodiments, the support structure 28 may be constructed of one or more polymers. In some embodiments, the support structure 28 may be monolithically formed as a single unit. In some embodiments, the support structure 28 may include multiple pieces coupled together.

In some embodiments, the support structure 28 may include a connector 32 configured to couple the fluid storage unit 20 to the adapter 18. In some embodiments, the connector 32 may include a male or female luer fitting. In some embodiments, after the priming of the catheter assembly, the fluid storage unit 10 may be removed from the catheter assembly. Thus, in some embodiments, the connector 32 may removably couple the fluid storage unit 20 to the adapter 18. In some embodiments, the fluid storage unit 20 may be needleless.

In some embodiments, the fluid storage unit 20 may include a one-way valve 34, which may be coupled to the support structure 28 and may allow the fluid 26 to flow in a single direction through the one-way valve 34. In some embodiments, the one-way valve 34 may be configured to allow the fluid 26 to flow out of the reservoir 24 and through the connector 32 in response to compression of a portion 36 of the barrier 22 aligned with the opening 30.

In some embodiments, the one-way valve 34 may prevent unintended fluid suck-back into the reservoir 24 after the fluid storage unit 20 is compressed. In some embodiments, the support structure 28 may reduce compression of another portion of the barrier 22, such as, for example, another portion 38, which may surround the opening 30. In some embodiments, an outer surface of the support structure 28 may contact or be disposed near an inner surface of the other portion 38 of the barrier 22. In some embodiments, an outer diameter 40 of the portion 36 of the barrier 22 aligned with the opening 30 may be less than an outer diameter 42 of the other portion 38 of the barrier 22. In some embodiments, the portion 36 of the barrier 22 aligned with the opening 30 may be disposed inwardly with respect to the other portion 38 of the barrier 22, which may be disposed around the portion 36 of the barrier 22 aligned with the opening 30. In some embodiments, the inward positioning of the portion 36 of the barrier 22 aligned with the opening 30 may prevent accidental activation of the fluid storage unit 20 during transportation, for example.

In some embodiments, the barrier 22 may fit tightly around the support structure 28. In some embodiments, the support structure 28 may be somewhat loosely fit within the barrier 22 such that the support structure moves 28 slightly with respect to the barrier 22. In some embodiments, the barrier 22 must be compressed above a threshold in order to release the fluid 26 from the reservoir. In some embodiments, the support structure 28 may prevent compression of the barrier 22 above the threshold except for at the portion 36 of the barrier 22 aligned with the opening 30. In some embodiments, the support structure 28 may be affixed to an inner surface of barrier 22 such that the fluid 26 is only disposed within the opening 30. In some embodiments, one or more of the following may be affixed to the inner surface of the barrier 22: a top surface 29, a bottom surface 31, and an outer side surface 33 of the support structure 28. In some embodiments, the support structure 28 may not be affixed to the barrier 22 such that fluid 26 may flow around the outer side surface of the support structure 28.

Figure 1E:
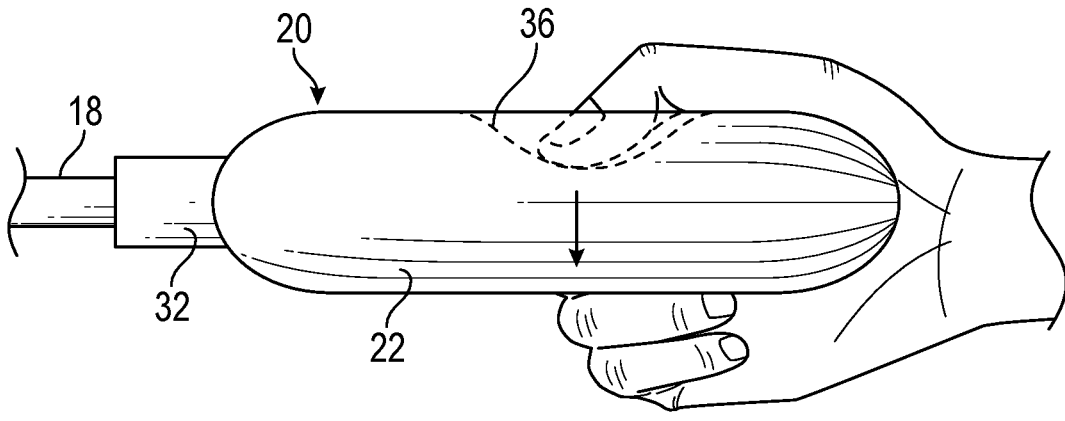
FIG. 1E is a side view of the fluid storage unit of FIG. 1A being compressed by a user, according to some embodiments.

Referring now to FIG. 1E, a user may pinch the fluid storage unit 20 to compress the fluid storage unit 20 and the reservoir 24 and release the fluid 26 to prime the catheter system 10. In some embodiments, the user may place his or her thumb on the portion 36 of the barrier aligned with the opening 30 during pinching.

In some embodiments, the fluid storage unit 20 may be pre-attached to the catheter hub 12 and/or pre-filled with the fluid 26, which may decrease a risk of contamination. In some embodiments, the catheter system 10 may be included in a kit, which may include the fluid storage unit 20 pre-attached to the catheter hub 12 and pre-filled with the fluid 26. In some embodiments, priming of the catheter system 10 via the fluid storage unit 20 may facilitate mobility of the patient after the catheterization and/or flexibility of the clinician during catheterization, as opposed to, for example, priming via the IV drip-chamber or pre-filled syringe.

Figure 2A:
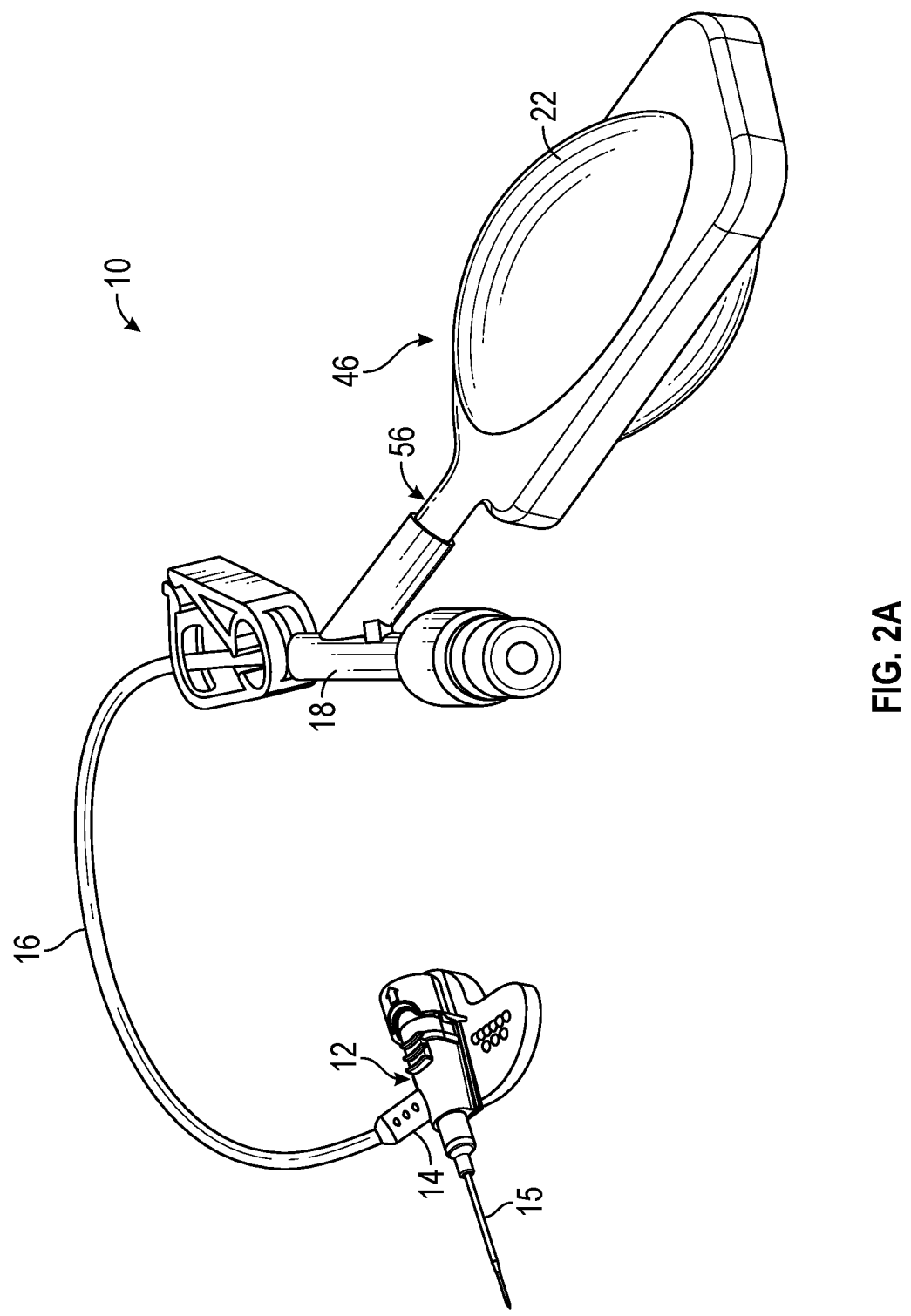
FIG. 2A is an upper perspective view of the catheter system having another example fluid storage unit, according to some embodiments.
Figures 2B, 2C:
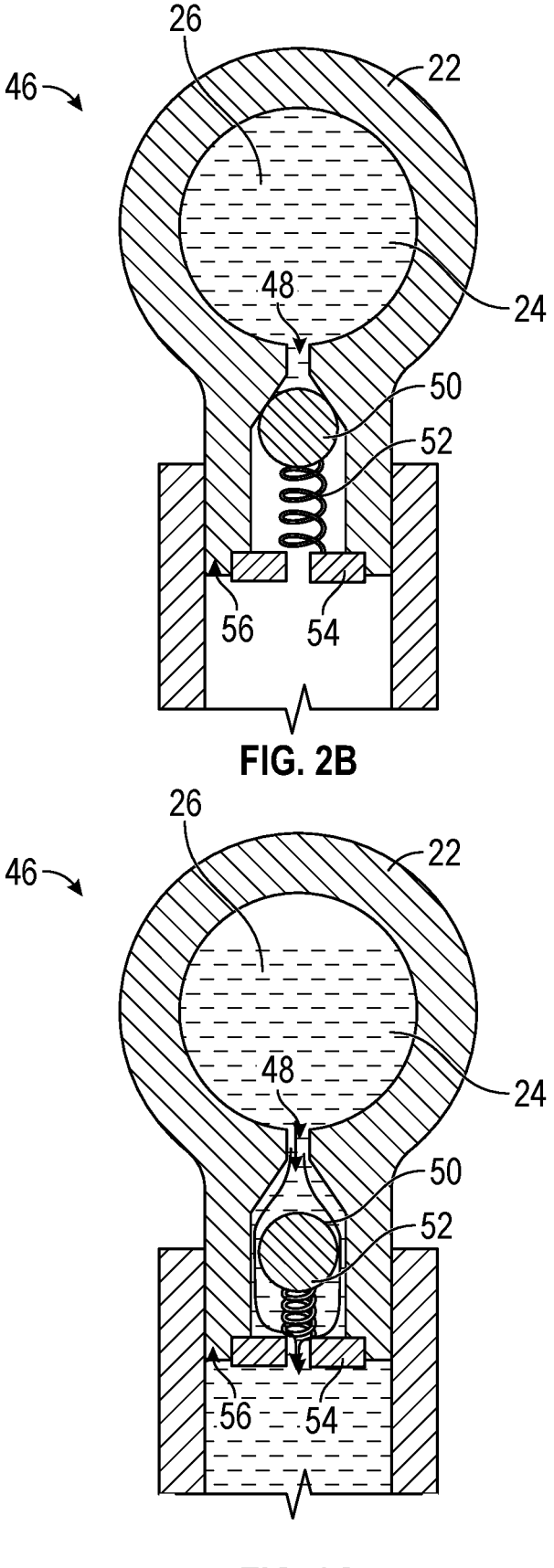
FIG. 2B is a cross-sectional view of the fluid storage unit of FIG. 2A, illustrating an example valve in a closed position, according to some embodiments.
FIG. 2C is a cross-sectional view of the fluid storage unit of FIG. 2A, illustrating the valve in an open position, according to some embodiments.

Referring now to FIG. 2A-2C, another fluid storage unit 46 is illustrated, according to some embodiments. In some embodiments, the fluid storage unit 46 may include or correspond to the fluid storage unit 20. In some embodiments, the fluid storage unit 46 may include one or more features of the fluid storage unit 20 and/or the fluid storage unit 20 may include one or more features of the fluid storage unit 46.

In some embodiments, the barrier 22 may include an aperture 48. In some embodiments, the fluid storage unit 46 may include a seal 50, which may be coupled to a spring 52. In some embodiments, in response to compression of the barrier 22, the fluid 26 may force the seal 50 distally to open the aperture 48 and compress the spring 52, as illustrated, for example, in FIG. 2C. In some embodiments, the spring 52 may be configured to return the seal 50 to a position sealing the aperture, as illustrated, for example, in FIG. 2B, in response to ceasing of compression of the barrier. In some embodiments, in response to ceasing of compression of the barrier 22, the barrier 22 may not decompress.

In some embodiments, the seal 50 may include a ball or another suitable shape configured to seal the aperture 48. In some embodiments, the fluid storage unit 46 may include a washer 54, which may be coupled to the barrier 22. In some embodiments, a distal end of the spring 52 may be coupled to the seal 50. In some embodiments, a proximal end of the spring 52 may be coupled to the washer 54. In some embodiments, in response to compression of the barrier 22, the fluid may flow through the aperture 48, around the seal 50 and the spring 52, and through the washer 54.

Figure 2D:
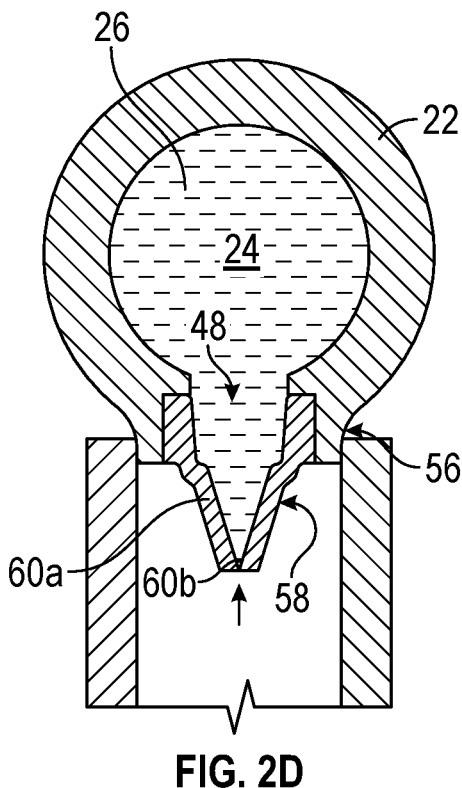
FIG. 2D is a cross-sectional view of the fluid storage unit of FIG. 2A, illustrating an example duckbill valve in a closed position, according to some embodiments.
Figure 2E:
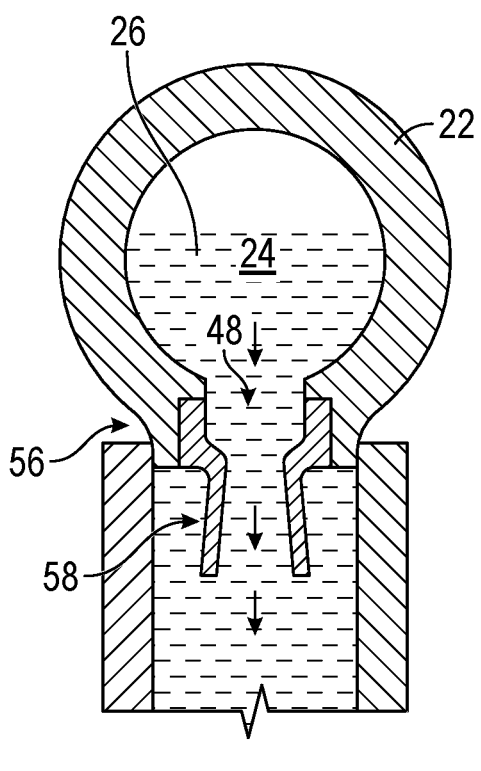
FIG. 2E is a cross-sectional view of the fluid storage unit of FIG. 2A, illustrating an example duckbill valve in an open position, according to some embodiments.

In some embodiments, a distal end of the barrier 22 may include a connecting portion 56 configured to couple to the adapter 18. In some embodiments, an outer surface of the connecting portion 56 may abut an inner surface of the adapter 18, facilitating a fluid seal. In some embodiments, the outer surface of the connecting portion 56 and/or the inner surface of the adapter 18 may be tapered. In some embodiments, the outer surface of the connecting portion 56 and/or the inner surface of the adapter 18 may be tapered at an angle within a range of about 5° to 10°. In some embodiments, the outer surface of the connecting portion 56 and/or the inner surface of the adapter 18 may be tapered at an angle of about 6°. In some embodiments, the outer surface of the connecting portion 56 may be tapered outwardly in a distal direction, and the inner surface of the adapter 18 may be tapered inwardly in a proximal direction, helping to create the fluid seal. Alternatively, in some embodiments, the outer surface of the connecting portion 56 may be tapered inwardly in a distal direction, and the inner surface of the adapter 18 may be tapered outwardly in a proximal direction, helping to create the fluid seal. In some embodiments, the Referring now to FIGS. 2D-2E, in some embodiments, the fluid storage unit 46 may include a duckbill valve 58, which may be coupled to the barrier 22. In some embodiments, the duckbill valve 58 may be configured to open in response to compression of the barrier 22 to allow the fluid 26 to flow out of the fluid storage unit 46. In some embodiments, a first flap 60a and a second flap 60b of the duckbill valve 58 may be configured to contact each other and seal the fluid storage unit 46 in response to ceasing of compression of the barrier 22. A non-limiting example of a duckbill valve is described in U.S. Pat. No. 9,126,012, filed Oct. 3, 2012, entitled "INTRAVENOUS CATHETER WITH DUCKBILL VALVE," which is hereby incorporated by reference in its entirety.

In some embodiments, the fluid storage unit 46 may be pre-attached to the catheter hub 12 and/or pre-filled with the fluid 26, which may decrease a risk of contamination. In some embodiments, the catheter system 10 may be included in a kit, which may include the fluid storage unit 46 pre-attached to the catheter hub 12 and pre-filled with fluid 26. In some embodiments, priming of the catheter system 10 via the fluid storage unit 46 may facilitate mobility of the patient after the catheterization and/or flexibility of the clinician during catheterization, as opposed to, for example, priming via the IV drip-chamber or pre-filled syringe.

Figure 3A:
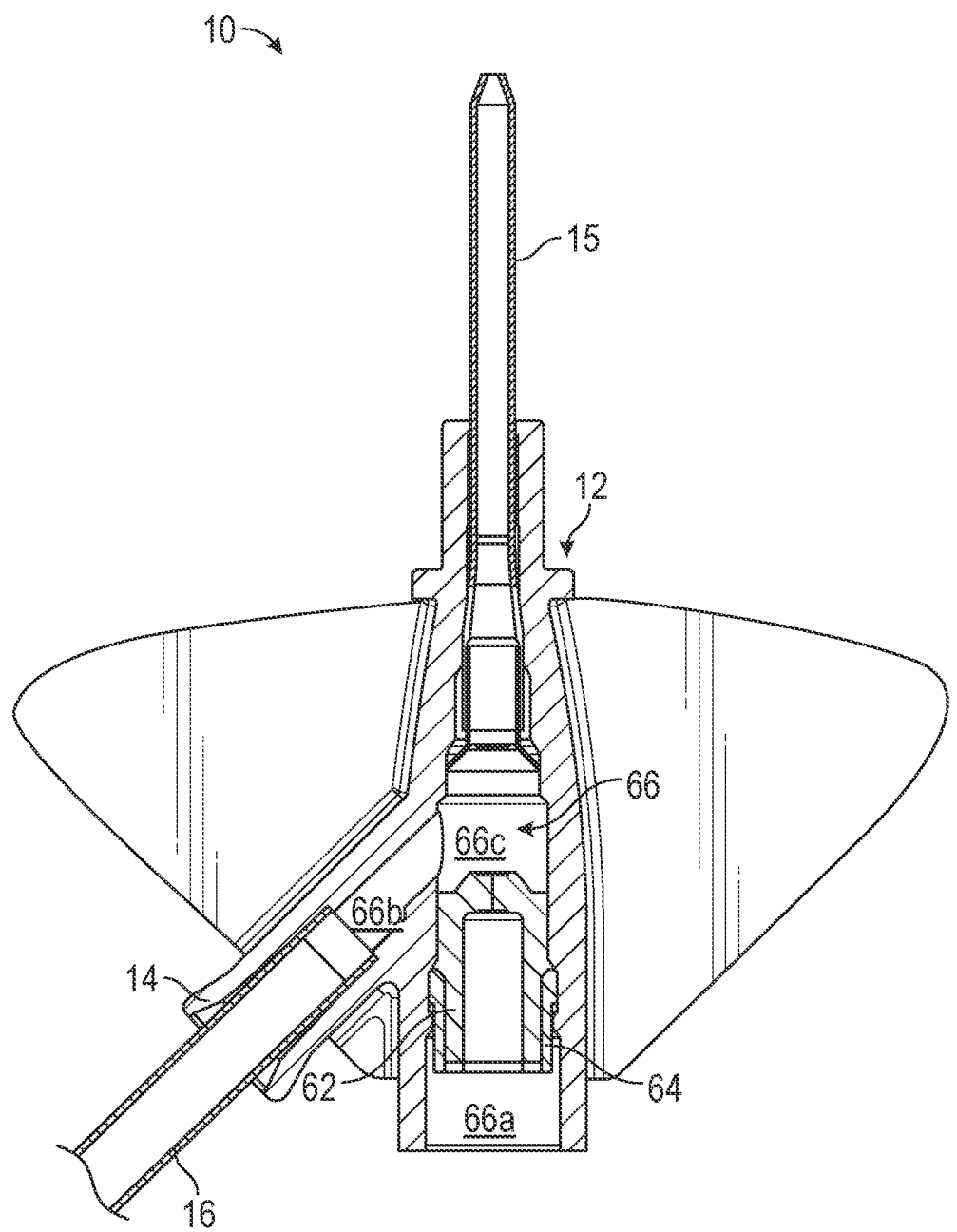
FIG. 3A is a cross-sectional view of an example catheter assembly of the catheter system of FIG. 1A, according to some embodiments.

Referring now to FIG. 3A, in some embodiments, the catheter hub 12 may include a septum 62 and/or a septum housing 64. It is contemplated that the septum 62 may include any number of types of septa and may be positioned at various locations with respect to the catheter hub 12. In some embodiments, the septum 62 may be disposed within a lumen 66 of the catheter hub 12. In some embodiments, the septum 62 may be at least partially disposed within the septum housing 64 and configured to at least substantially seal the lumen 66 of the catheter hub 12. In some embodiments, the septum housing 64 may prevent dislodgement or destabilization of the septum 62, thereby preventing leakage of fluid from the lumen of the catheter hub 12.

In these and other embodiments, the lumen 66 of the catheter hub 12 may include a first lumen 66a and/or a second lumen 66b. In some embodiments, the proximal end of the catheter hub 12 may form the first lumen 66a and/or the side port 14 may form the second lumen 66b. In some embodiments, the first and second lumens 66a, 66b may join at a common lumen 66c. In some embodiments, the first lumen 66a may be generally aligned with the common lumen 66c. In some embodiments, the septum 62 and/or the septum housing 64 may be disposed in the first lumen 66a.

In some embodiments, the second lumen 66b of the catheter hub 12 may be coupled with the fluid storage unit 20 via the extension tube 16 that may extend from the side port 14 of the catheter hub 12. In some embodiments, the extension tube 16 may extend from the proximal end of the catheter hub 12 or another port of the catheter assembly. In some embodiments, the extension tube 16 may include a clamp.

Figure 3B:
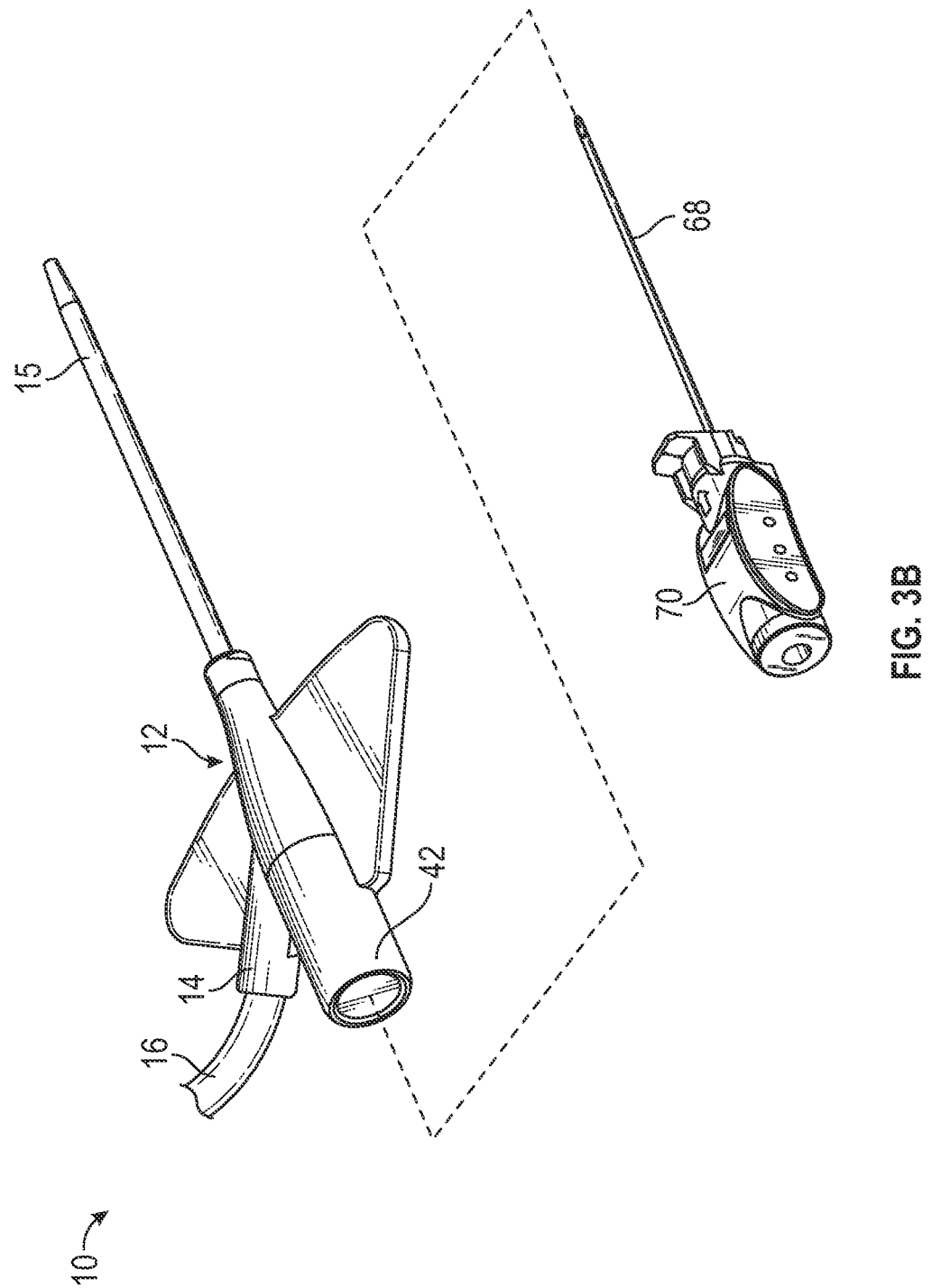
FIG. 3B is an upper perspective view of an example needle hub configured to be coupled with the catheter assembly of the catheter system of FIG. 1A, according to some embodiments.

Referring now to FIG. 3B, in some embodiments, an introducer needle 68 of the catheter assembly may be withdrawn through the catheter hub 12 after insertion of the catheter 15 into the vasculature of the patient. In some embodiments, the introducer needle 68 may extend distally from a needle hub 70. In the closed IV catheter assembly, when the introducer needle is withdrawn through the catheter hub 12, the first lumen 66a, which may correspond to a "needle channel," may be closed off by the septum from an external environment surrounding the catheter hub 12. Thus, the septum may at least substantially seal the proximal end of the catheter hub 12 and prevent fluid from exiting the catheter hub 12 through the proximal end of the catheter hub 12. In some embodiments, the fluid pathway of the catheter assembly 14 during fluid priming and/or infusion may extend through the side port 14 and not the proximal end of the catheter hub 12.

All examples and conditional language recited herein are intended for pedagogical objects to aid the reader in understanding the invention and the concepts contributed by the inventor to furthering the art, and are to be construed as being without limitation to such specifically recited examples and conditions. Although implementations of the present inventions have been described in detail, it should be understood that the various changes, substitutions, and alterations could be made hereto without departing from the spirit and scope of the invention.

The invention claimed is:

1. A catheter priming apparatus, comprising:
   a barrier forming a reservoir;
   fluid disposed within the reservoir;
   an annular support structure disposed within the reservoir, the annular support structure defining:
   an opening extending vertically completely through the support structure along a vertical axis of the support structure, the support structure annularly surrounding the opening; and
   a channel extending radially completely through the annular support structure along an axis at least substantially perpendicular to the vertical axis of the support structure and in fluid communication with the opening, wherein the support structure comprises a connector configured to couple the catheter priming apparatus to a catheter system, wherein the barrier surrounds the support structure such that the support structure is disposed within the barrier;

a valve coupled to the support structure and configured to allow the fluid to flow out of the reservoir through the connector in response to compression of a portion of the barrier aligned with the opening, wherein the valve seals the fluid within the reservoir proximal to and contacting the valve.

2. The catheter priming apparatus of claim 1, wherein the valve comprises a seal coupled to a spring, wherein in response to compression of the barrier, the fluid forces the seal distally to compress the spring and open the valve.

3. The catheter priming apparatus of claim 2, wherein the seal comprises a ball.

4. The catheter priming apparatus of claim 2, wherein the spring is configured to return the seal to a position sealing the reservoir in response to ceasing of compression of the barrier.

5. The catheter priming apparatus of claim 2, further comprising a washer coupled to the barrier, wherein a distal end of the spring is coupled to the seal, wherein a proximal end of the spring is coupled to the washer.

6. The catheter priming apparatus of claim 5, wherein in response to compression of the barrier, the fluid flows around the seal and the spring and through the washer.

7. The catheter priming apparatus of claim 5, wherein a distal end of the barrier comprises a connecting portion configured to couple to a catheter system, wherein an outer surface of the connecting portion is tapered.

8. The catheter priming apparatus of claim 7, wherein the outer surface of the connecting portion is tapered at an angle of about six degrees.

9. The catheter priming apparatus of claim 1, wherein the valve comprises a duckbill valve coupled to the barrier, wherein the duckbill valve is configured to open in response to compression of the barrier to allow the fluid to flow out of the catheter priming apparatus.

10. The catheter priming apparatus of claim 9, wherein a first flap and a second flap of the duckbill valve are configured to contact each other and seal the catheter priming apparatus in response to ceasing of compression of the barrier.

11. The catheter priming apparatus of claim 1, wherein the support structure reduces compression of another portion of the barrier.

12. The catheter priming apparatus of claim 1, wherein the barrier comprises a film.

13. The catheter priming apparatus of claim 1, wherein the fluid comprises saline.

14. The catheter priming apparatus of claim 1, wherein the connector comprises a male luer fitting.

15. The catheter priming apparatus of claim 1, wherein the support structure is rigid.

16. A catheter priming apparatus, comprising:

a barrier forming a reservoir;

fluid disposed within the reservoir;

a connector configured to couple the catheter priming apparatus to a catheter system;

a support structure disposed within the reservoir, wherein the support structure is annular to form an opening extending vertically completely through the support structure along a vertical axis of the support structure, the support structure annularly surrounding the opening; and a channel extending radially completely through the annular support structure along an axis at least substantially perpendicular to the vertical axis of the support structure and in fluid communication with the opening, wherein the barrier surrounds the support structure such that the support structure is disposed within the barrier, wherein the opening is oriented generally perpendicular to a longitudinal axis of the catheter priming apparatus and wherein the barrier at least partially surrounds the connector;

a valve configured to allow the fluid to flow out of the reservoir through the connector in response to compression of the barrier, wherein the valve seals the fluid within the reservoir proximal to and contacting the valve and within the opening.

17. The catheter priming apparatus of claim 16, wherein the valve is coupled to the barrier.

18. The catheter priming apparatus of claim 16, wherein the valve comprises a seal coupled to a spring, wherein in response to compression of the barrier, the fluid forces the seal distally to compress the spring and open the valve.

19. The catheter priming apparatus of claim 16, wherein the valve comprises a duckbill valve coupled to the barrier, wherein the duckbill valve is configured to open in response to compression of the barrier to allow the fluid to flow out of the catheter priming apparatus.

20. The catheter priming apparatus of claim 16, wherein the valve comprises a one-way valve.

* * * * *